(12) United States Patent
Page et al.

(10) Patent No.: US 7,179,596 B2
(45) Date of Patent: Feb. 20, 2007

(54) BIOLOGICAL PARTICULATE MATTER ANALOGUE

(75) Inventors: Andrew E. Page, Kansas City, MO (US); Kelly L Brown, Kansas City, MO (US); David S. Alburty, Drexel, MO (US); Robert C. Huebner, Liberty, MO (US)

(73) Assignee: Sceptor Industries, Inc., Kansas City, MO (US)

( * ) Notice: Subject to any disclaimer, the term of this patent is extended or adjusted under 35 U.S.C. 154(b) by 0 days.

(21) Appl. No.: 10/248,775

(22) Filed: Feb. 17, 2003

(65) Prior Publication Data

US 2004/0191770 A1 Sep. 30, 2004

(51) Int. Cl.
*C12Q 1/68* (2006.01)
*C12Q 1/04* (2006.01)
*C07K 4/04* (2006.01)
*C07H 21/02* (2006.01)
*C07H 21/04* (2006.01)

(52) U.S. Cl. .................. 435/6; 530/350; 536/23.1; 435/34

(58) Field of Classification Search ............ 435/252.1, 435/252.3, 252.31
See application file for complete search history.

(56) References Cited

U.S. PATENT DOCUMENTS

| | | | | |
|---|---|---|---|---|
| 5,382,512 A | * | 1/1995 | Smethers et al. | 435/6 |
| 5,434,068 A | * | 7/1995 | Brooks et al. | 435/199 |
| 5,840,312 A | * | 11/1998 | Mock et al. | 424/200.1 |
| 5,851,794 A | * | 12/1998 | Guss et al. | 435/69.1 |
| 2003/0203362 A1 | * | 10/2003 | Hunter-Cevera et al. | 435/6 |

FOREIGN PATENT DOCUMENTS

WO WO 02/18635 A2 3/2002
WO WO 03/050556 A2 6/2003

OTHER PUBLICATIONS

Huang et al., Anal. Biochem., vol. 237, pp. 115-122 (1996).*
Polysciences, In. Technical Data Sheet 238.*
Kradtap Supaportn et al.; "Bugbead": An Artificial Microorganism Model used as a Harmless Stimulant for Pathogenic Microorganisms; XP-002322555, Analytica Chimica Acta; Oct. 12, 2001; pp. 13-26; vol. 444, No. 1; Elservier Science B.V.
Makino, S. I. et al.; "Detection of anthrax spores from the air by real-time PCR"; XP-00232267, Letters In Applied Microbiology; Sep. 3, 2001; pp. 237-240; vol. 33, No. 3; The Society for Applied Microbiology.
Flick-Smith, H. C. et al; "Mucosal or Parenteral Administration of Microsphere-Associated Bacillus Anthracis Protective Antigen Protects Against Anthrax Infection in Mice"; XP-002977234, Infection and Immunity; Apr. 2002; pp. 2022-2028; vol. 70, No. 4; American Society for Microbiology, Washington, D.C.
Brosseau, L. M. et al.; "Differences in Detected Fluroescence among Several Bacterial Species Measured with a Direct-Reading Particle Sizer and Fluorescence Detector"; XP-002322625, Aerosol Science and Technology; Jun. 6, 2000; pp. 545-558; vol. 32, No. 6.
Weimer, B. C. et al.; "Solid-phase Capture of Proteins, Spores, and Bacteria"; XP-002322626, Applied and Environmental Microbiology, Mar. 2001; pp. 1300-1307; vol. 67, No. 3; Applied and Environmental Microbiology.

* cited by examiner

*Primary Examiner*—Nancy Vogel
(74) *Attorney, Agent, or Firm*—Shook, Hardy & Bacon L.L.P.

(57) ABSTRACT

The present invention provides a biological particle analogue, or biological analogue, that simulates a chosen biological organism or compound. The biological analogue includes a first portion that is not, in and of itself, recognized by the biological detection system, and a second portion, which provides the properties necessary for recognition by the detection system, carried by the first portion. The biological analogue is constructed in such a way as to include some important characteristics of the chosen biological organism or compound, while excluding other undesirable characteristics of the chosen biological organism or compound. The present invention is useful in testing a variety of biological detection systems.

35 Claims, No Drawings

BIOLOGICAL PARTICULATE MATTER ANALOGUE

BACKGROUND OF INVENTION

This invention relates generally to a device and method for emulating biological organisms, biological particles, or biological molecules and, specifically, to an analogue for biological organisms, biological particles, or biological molecules that is constructed in such a way as to include some important characteristics of that organism, particle, or molecule while excluding other undesirable characteristics.

In recent years, as the level of sophistication in the field of biotechnology has increased, the threat of biological weapons use by terrorist groups and rogue nations has also increased. Many of the basic methodologies involved in the production of biological weapons, as well as the basic starting materials, are more readily available and less expensive than those required for nuclear or conventional weaponry. As the threat of the use of biological weapons grows, it is imperative that means for early detection and identification of biological warfare agents are provided.

Some devices and methods for the detection and identification of potential biological warfare agents are known in the art. The U.S. Postal Service, for example, is in the process of evaluating Northrop Grumman's Biological Detection System for use in some of its facilities. Other detection systems are likewise available from other manufacturers. Verifying that these systems are operating properly and will detect the presence of biological warfare agents, however, presents a challenge.

Devices like the Northrop Grumman Biological Detection System are generally tested for proper operation after installation and periodically thereafter. The best way to test such a device is to simulate a biological event (i.e. simulate the dispersal of a biological warfare agent in the environment of the detection system). From a practical standpoint, however, it is not feasible to release a potential biological warfare agent, such as anthrax, into a facility or outdoors environment for obvious reasons. Thus, a means of testing biological detection systems without releasing potentially dangerous agents into the air is required.

One testing method used in the past has been to release some sort of surrogate biological organism in place of the dangerous biological agent to be detected by various biological detection systems. In the Northrop Grumman device mentioned above, for example, the organism *Bacillus globigii* is currently being used for testing purposes. Use of an organism such as *B. globigii* is far less dangerous than using a potentially deadly agent such as anthrax, however any use of a living organism presents certain problems. The risk of infection always remains when a live biological organism is used in testing equipment in a building or other location. Further, even if infection does not result from such a use, there is a risk of allergic response to the organism on the part of persons in the area both during and after the testing. Also, immunocompromised individuals may be particularly susceptible to the ill effects of any remaining biological organisms. During the testing, persons in the area may wear personal protective equipment (PPE) to minimize such risks, however some microorganisms are notoriously persistent in the environment and may linger in the area after the testing is concluded and regular personnel have returned to the facility. Members of the *Bacillus* genus, for example, are particularly persistent due to the formation of endospores. Even if these immediate negative effects are not apparent, it is undesirable to allow unchecked growth of a microorganism within a facility after such a test has been conducted. A full decontamination procedure after every test of the biological detection system is time-consuming, difficult to verify, and expensive. Such a decontamination procedure is not practical. In addition, even when such decontamination procedures are undertaken, the decontamination is never perfect and unwanted biological organisms may still persist.

Finally, testing with surrogates may not be a true test of a system since the testing program or kit may need to be altered or replaced to detect a surrogate instead of the biological warfare agents a system is designed to identify. Specialty kits may be needed for various testing scenarios. A biological analogue made with markers for an actual biological warfare agent could to used to safely do a real test of the system and could even be employed by inspector or oversight personnel to test the proficiency of in-place systems and their operators.

There is, therefore, a great need for some sort of device and/or method that will allow accurate testing of a biological detection system without the use of living organisms. Such a device and method must simulate a true biological organism dispersal event as closely as possible in order to provide the accurate results needed to ensure that a biological detection system is working properly and will perform in the event of a true biological warfare event.

SUMMARY OF INVENTION

In view of the foregoing, the present invention provides a biological particle analogue that can be safely used to simulate a predetermined biological material for purposes of testing a biological detection system, or for other applications.

The present invention is a manufactured biological analogue that includes more than one important characteristic from the suite of characteristics possessed by a specific biological material that it is meant to simulate, while excluding at least one undesirable characteristic. In a preferred embodiment, a biological analogue of the present invention includes a first portion and second portion, where the second portion is carried by the first portion, that can be recognized by a biological detection system. The second portion may be DNA, RNA, PNA (pentose nucleic acid), protein, or other biologically active molecules, such as dipicolinic acid, carbohydrates, lipids or antibodies. In one alternative embodiment of the present invention, the second portion of the biological analogue includes at least one fluorophore, allowing the biological analogue to simulate the fluorescing behavior of a chosen biological organism or compound.

In another embodiment of the present invention, the biological analogue may include DNA, or another biologically active molecule, associated with a carrier such as oleic acid (the first portion in this embodiment) or other semivolatile or volatile liquid, thereby producing an aerosol.

A biological analogue constructed in accordance with the present invention may be designed to simulate directly a biological organism that is used in the context of biological warfare, or it can be designed to simulate a so-called surrogate organism such as *B. globigii*, commonly used to test biological detection systems.

Biological analogues can also be used to test the effect of a biological warfare agent release into buildings, subways, municipal water systems, and other locations or public health systems that may be the target of a biological warfare attack. The time of dispersion, time course, and overall pattern of dispersion of a biological agent can be discerned so that protective measures can be developed. In the case of water systems, biological analogues can be developed such that the DNA or RNA is encapsulated in a material that will tolerate the aqueous conditions long enough for testing to occur, then biodegrade through normal processes or be destroyed by normal water treatment processes.

The second portion of the biological analogue can be attached to or otherwise carried by the first portion of the biological analogue through covalent or ionic linkages, or, in one embodiment of the present invention, through streptavidin/biotin linkages. The second portion could also be encapsulated within the first portion of the biological analogue. This may present certain advantages since it could protect the second portion from the environment until it is released from the encapsulation material for detection.

In another embodiment of the present invention, the first portion of the biological analogue is paramagnetic.

The biological analogue described herein, and its method of use, is invaluable in testing and calibration of biological detection systems. The biological detection systems that can be calibrated or tested using a biological analogue of the present invention are not limited to biological warfare-related systems but may include food screening systems or any other system wherein a biological organism is traditionally used for testing or calibration. The present invention provides a means of conducting required testing without the use of live biological organisms. Other and further advantages of the present invention are set forth in the description and appended claims.

DETAILED DESCRIPTION

The constructs of the present invention serve as analogues or surrogates (hereinafter termed "biological analogues") of biological materials, and the present invention also relates to a method of using such biological analogues to safely simulate biological materials. As used herein, the term "biological material" includes any biological particle, organism or biologically active molecule. The biological analogue is preferably of the same aerodynamic diameter as its biological counterpart and has a portion of DNA or RNA from the biological particle attached thereto. The term "aerodynamic diameter" is an expression of the aerodynamic behavior of an irregularly shaped particle in terms of the diameter of an idealized particle; that is, aerodynamic diameter is the diameter of a sphere of unit density that has aerodynamic behavior identical to that of the particle in question. Thus, particles having the same aerodynamic diameter may have different dimensions and shapes.

In addition to DNA or RNA, a portion of a protein toxin or portions of other biological molecules may be included in the corresponding biological analogue. Biological analogues can be designed to simulate specific bacterial or viral organisms or any other biological materials of interest.

The biological analogues produced in accordance with the teachings of the present invention preferably have a first portion, such as a particle or bead that carries a second portion, such as DNA or RNA (or other biologically active portion) associated with the biological material of interest. As used herein, the phrase 'associated with' means that the biological material is commonly found as part of the biological organism or compound in question. For example, a biological material associated with a biological organism may be a viral protein coat, a cell surface receptor, a portion of the genome of an organism, a compound, or any other biological material found on, within, or linked to the biological organism or compound.

One feature of the design of the biological analogue is that it is the second portion used in the construction of the biological analogue that provides the means for identifying the biological analogue as the biological material. For example, one way of making a Bg (*Bacillus globigii*) biological analogue is by constructing it so that genomic DNA from *B. globigii* is attached to the bead or other carrier. Alternatively, a fragment of DNA that is unique to Bg (either synthetic or purified from the genome of Bg) is attached to the bead or other carrier. The beads are disseminated and collected, and an assay that has been developed to be specific to Bg DNA is used to test for the presence of Bg (either the genome or the fragment of DNA that has been attached to the beads). In this way, the biological analogues are designed specifically to meet any and all test requirements. The development of biological analogues with second portions from actual biological warfare agents allows for testing of detection systems while they are being run as they are designed to run and not in an artificial modified testing mode. These types of biological analogues can be safely used in the field to do proficiency testing of in-place systems and their operators.

A biological analogue may also be provided including wholly synthetic DNA, RNA, protein or other material, as well as with molecules that are partially synthetic and partially taken from the biological organism or compound of interest. The amount of DNA, RNA or other molecules attached to the biological analogue varies depending on the organism being simulated and the detection system being tested or calibrated. The amount of such molecules used, in relation to the number of biological analogues made, will most often be proportionately similar to the molecule-to-organism ratio in the actual organism.

The DNA, RNA or other molecule that makes up the second portion of the present invention may be carried by the first portion of the present invention because of covalent, ionic or other type of binding. The first portion of the biological analogue may be constructed from a number of suitable materials. In a preferred embodiment, the present invention includes a polystyrene latex bead (the first portion) with an oligonucleotide, longer DNA fragment, or genomic DNA covalently (the second portion) linked thereto. Polystyrene latex beads are commercially available in a wide range of sizes from submicron to about 100 microns.

Another embodiment of the present invention includes microencapsulation of the second portion. This protects the second portion from the environment until released for detection. Microcapsules can be made in a wide range of sizes to suit the scenario in which the biological analogues are to be used.

Biological analogues made by microencapsulation of the second portion have certain advantages over the non-encapsulated embodiments. First, there exists a range of materials available for use with microencapsulation, each with different properties that allow the practicioner to make biological analogues of various sizes, hydrophobicity, surface charges, densities, or other desirable characteristics. Second, microencapsulation is extremely useful in the case of RNA biological analogues because RNA may not be very stable in the environment unless it is protected in some manner. Microencapsulation, or other coating methods, can protect the RNA until the microcapsules are broken or dissolved for detection. Finally, microencapsulation can be used to encapsulate all types of second portions of the biological analogue, including DNA, RNA, protein, protein fragments, and other biomolecules.

The second portions are encapsulated by mixing them with the microencapsulation materials (which are the first portion in this embodiment of the invention) and performing microencapsulation in the presence of the second portions. The resulting microcapsules contain the second portion that was present during their formation. It is possible to re-encapsulate the microcapsules, giving them an outer coat with desirable properties such as acid resistance, a desired charge, water insolubility, or to simulate the cell wall or spore coat of a microorganism.

One example of a situation in which a biological analogue constructed in accordance with the teachings of the present invention is useful concerns the U.S. Postal Service. As noted above, the Postal Service is evaluating the Northrop Grumman Biological Detection System for screening of flat mail for biological agents. Currently, that detection system is being tested with *Bacillus globigii*. The Postal Service has a need for periodic testing and inspection of the detection system but will not allow the use of any bacteria within its facilities. Use of live bacteria is problematic because of the infectious, allergenic or toxic nature of biological organisms. Further, some biological organisms can persist for a long time after use and there may be problems associated with unwanted growth of these organisms. For the Postal Service, it is imperative that its Biological Detection System be tested without using living organisms:

In accordance with the teachings of the present invention, a *B. globigii* biological analogue can be constructed by linking the required portion of *B. globigii* DNA (the second portion) to a polystyrene latex bead (the first portion) of nominally the same aerodynamic diameter as *B. globigii*. Once the appropriate biological analogue is in hand, it is injected into the Biological Detection System as an aerosol and transported through the system. The Biological Detection System collects the *B. globigii* biological analogue in the same manner in which it would collect an actual bacterial sample from the air within and surrounding the mail. In short, the *B. globigii* biological analogue acts in much the same manner as an actual *B. globigii* spore. Once the biological analogue is captured by the Biological Detection system, a sample of the collection fluid can be analyzed. The DNA linked to the polystyrene latex bead is removed by sonication during normal sample processing, providing the free DNA for analysis.

In addition to scenarios in which a biological analogue is designed to simulate one specific biological organism or compound, biological analogues can be produced that contain target sequences from multiple biological organisms or compounds of similar aerodynamic diameters. In this way, a single type of biological analogue can be used to test detection systems for multiple biological organisms or compounds.

In addition to the target sequence for the biological organism or compound, unique, non-naturally occurring synthetic DNA may also be attached to biological analogues. The addition of unique synthetic DNA has several advantages. By analyzing for the unique synthetic DNA the biological analogues can be differentiated from the real biological organism or compound. The addition of unique synthetic DNA also allows for individual coding of manufactured lots of biological analogues. These DNA codes can be matched with the purchaser of each lot of biological analogues sold. Through DNA analysis, inappropriate use of biological analogues can then be traced to the purchaser of that lot.

There are a number of alternative constructions available for the first portion of the biological analogues of the present invention. Silica spheres, paramagnetic spheres, microencapsulated spheres, or other solid or liquid particles can be substituted for polystyrene latex beads, for example. Other suitable bead compositions include, but are not limited to, polystyrene styrene/divinylbenzene copolymer, polymethylmethacrylate, polyvinyltoluene styrene/butadiene copolymer, styrene/vinyltoluene copolymer, vinyl carboxylic acid/styrene copolymer, and styrene/maleic anhydride copolymer, amino-modified microspheres, and carboxylate-modified microspheres. A number of additional constructions are described below. It should be noted, however, that many other modifications and alternative constructions will be readily apparent to one of ordinary skill in the art upon reading the disclosure contained herein.

Attachment of DNA to beads via streptavidin/biotin linkage provides a more robust biological analogue than does simple ionic-based attachment of DNA to silica spheres or polystyrene latex beads. This represents one alternative construction of a biological analogue of the present invention. Polystyrene beads are coated first with streptavidin and then with biotinylated *B. globigii* DNA. Each bead receives an average of five genomic equivalents of DNA. Further, the DNA attaches to the beads according to a Poisson Distribution such that very few beads have no genome equivalents. It is proven that sonication will disrupt the streptavidin/biotin linkage. Therefore, these linkages may not be suitable for use in systems wherein sonication occurs unless it is desired that the linkages be broken. The linkages do, however, allow the biological analogue to more closely simulate a real biological agent in detection systems that utilize sonication to disrupt microorganisms for subsequent identification.

Biological analogues may also be constructed based upon dipicolinic acid as the second portion. Dipicolinic acid is a biological molecule unique to the bacterial endospore. Using dipicolinic acid as a biomarker on a biological analogue construction allows that particular biological analogue to be used as a non-biological surrogate for spore-forming bacteria such as *B. anthracis*, the causative agent of anthrax. The use of dipicolinic acid also allows the biological analogue to be used in situations requiring non-DNA based methods of detection, such as ELISA-based methods. Various procedures could be adapted for attaching dipicolinic acid to polystyrene beads. A particular protocol for attachment of dipicolinic acid to the biological analogue may be chosen based upon the strength of the attachment, the tolerance of the attachment to various collection means, the simplicity of the protocol, the availability of materials, and the costs associated with a particular protocol.

RNA-based biological analogues are important for simulation of viral dissemination events because many viruses have RNA genomes. Methods for creating RNA-based biological analogues are similar to those for creating DNA-based biological analogues described above. Microencapsulation and other methods of coating are particularly attractive for RNA biological analogues because of the more labile nature of RNA when exposed to the environment. Other known techniques for protecting RNA or other biomolecules can be used in conjunction with the biological analogues of the present invention.

Biological analogues can also be constructed having a fluorescent signature matching that of a certain biological agent of interest. For example, some systems detect anthrax through laser-induced fluorescence of the organism. A biological analogue can be constructed that simulates the fluorescence of anthrax, thereby allowing the biological analogue to replace anthrax or biological surrogates used during system checks or testing.

In addition to the above constructions, paramagnetic beads may be used to enhance the usefulness of the biological analogues. Paramagnetic beads coated with streptavidin and biotinylated *B. globigii* DNA are particularly useful. Such paramagnetic beads are readily concentrated to verify their presence in a dilute sample or to differentiate them from real bacteria. For example, when a 10 mL volume of collection fluid is exposed to a magnet, the paramagnetic beads are drawn to the magnet, thereby concentrating them into a volume of 100–200 µL prior to extraction and analysis. This allows the presence of the biological analogue to be distinguished from the presence of actual bacteria when such an analysis is required. For example, shortly after testing or calibration of a biological detection system, the system may indicate the presence of bacterial agents in the testing area. Such an indication could be due to a true biological event or, instead, could be due to residual biological analogues in the environment creating a 'false positive'. If the biological analogue beads are paramagnetic, any low-level residual amount could be easily concentrated and detected. They also provide an easy means of concentrating biological analogues in a reference sampler during a low-level release scenario. Further, such magnetized biological analogues allow for easy cleanup after a testing scenario because they are easily removed by magnetic means. Use of such paramagnetic beads is possible with any of the biological analogue constructions described above, and in other biological analogue constructions that will be readily apparent to those of ordinary skill in the art upon reading this disclosure.

The second portion of the biological analogue may also be aerosolized by dissemination of the second portion in a carrier (a first portion) such as, for example, oleic acid or other semivolatile or volatile liquid. A biological analogue constructed in this manner is useful for testing biological detection systems designed to detect aerosolized biological materials.

Numerous devices for detection of biological organisms and/or compounds are currently available. For each existing device, the specific method of detection used is known (i.e. it is known how the device detects and/or identifies biological organisms or compounds). Thus, given knowledge of any specific detection system, and the contents of the present disclosure, a biological analogue can be constructed for use with any system. Likewise, as new detection systems are developed over time, biological analogues can be constructed for those systems given knowledge of how those systems work and the contents of the present disclosure. The following paragraphs provide information on a few exemplary detection systems.

MesoSystems (Kennewick, Wash.) sells the BT-500 and BT-550 BioCapture™ detection systems. The systems use Tetracore BTA™ (Bio Threat Alert) test strips. These strips utilize an antibody-based detection system that provides a color indication when a target organism or compound is detected. Toxins or microbes currently detected by the system are anthrax, ricin, botulinum, and staphylococcal enterotoxin. Depending on which of these is to be detected, a different antibody is used in the test system. A biological analogue for use in testing this system, and constructed in accordance with the teachings of the present invention, would include a biologically active portion that is capable of being bound by the specific antibodies used in the test system.

The Portal Shield biological chemical detection system manufactured by Sentel (Alexandria, Va.) also uses immunological methods for detecting various biological and chemical agents. The system uses a particle counter to trigger the device. Multiple Portal Shield systems are positioned around military installations and are networked together to provide quick response to attack and to reduce the number of false alarms. Biological analogues designed for use in testing this system would preferably be of about the same size as the particles being emulated. Again, since the specific immunological assays used are known, one could construct biological analogues that react accordingly. In addition to specifically testing the detectors response to the biological analogue, releases at various locations around an installation would test the systems response to attack.

Texas Instruments (Dallas, Tex.) manufactures the SPREETA surface plasmon resonance biodetector. The biodetector is able to measure properties such as refractive index changes, avidin-biotin binding, antibody-antigen dissociation kinetics, thickness of insulators, refractive index of thin dielectrics, specific detection of small molecules, protein binding, concentrations of analytes, attachment of DNA complements, and mixture proportions. Depending on the specific target of the detection system, the properties measured may varied. To test the capabilites of the SPREETA detection system, a biological analogue can be designed to simulate the characteristics for which the system is screening. Since, for any given version of the SPREETA system, it will be known what the system is looking for, a biological analogue can be designed accordingly. For example, if the SPREETA system is looking for specific small molecules, then those are the molecules that make up the biologically active portion of the biological analogue.

Advanced Analytical Technology, Inc. (AATI; Ames, Iowa) has developed a fluorescence-tagged flow cytometer for low-level microbe detection. Each species of microbe to be detected will give a unique combination of side scatter and fluorescence detector responses. In order to construct a biological analogue suitable for testing the AATI device, a biological analogue is constructed that provides the same set of side scatter and fluorescence detector responses as the corresponding microbe.

The Northrop Grumman device, mentioned above, uses a DNA-based detection system. The following examples detail the construction of a biological analogue for *B. globigii* suitable for use with the Northrop Grumman system.

EXAMPLE

As indicated above, the U.S. Postal Service requires a means of conducting post-installation and periodic tests of its Biological Detection System. *B. globigii* is commonly used as a biological warfare surrogate organism for such purposes, however the U.S. Postal Service will not allow a live organism to be used in testing on its premises. The example now described provides a *B. globigii* biological analogue for use in testing such Biological Detection Systems.

Attachment of genomic Bg to silica beads by ionic-based interactions

Because of the need to simulate the *B. globigii* endospore as closely as possible, it was important to determine how many genome equivalents of *B. globigii* genomic DNA to attach to each biological analogue bead. One *B. globigii* endospore contains one genome of *B. globigii* DNA. The DNA to be attached to the biological analogue beads cannot, however, simply be added in an amount that constitutes enough DNA to attach one genome equivalent to each biological analogue bead. This is because the binding occurs in a Poisson Distribution so that, even if the DNA binds with 100% efficiency, a large number of biological analogue beads (around 36% or more) will receive no DNA at all.

If sufficient DNA is added to provide five genomic equivalents for each biological analogue beads will have no DNA attached. Around 3%, or slightly more, will have received one genomic e 9% receive two genomic equivalents, 14% receive three genome equivalents, and so forth, as sh PCR analysis further indicated that very little DNA was removed during the initial washing procedure (approximately 1% or less). The PCR reaction conducted with the first rinse from the washing procedure described above was inhibited, preventing a direct determination of how much DNA was washed off of the biological analogue beads during the first rinse, however the high DNA yields in the extraction and the very low amounts of DNA observed in Rinses 3–9 (only the odd numbered rinses were analyzed, see Table 2) indicate that the rinsing steps, including Rinse 1, removed very little DNA. The final extraction, which yielded 33% of the DNA, indicated an overall recovery of

TABLE 1

Poisson Distribution for Five Genome Equivalents of DNA/Bead

| | DNA copies | | | | | | | | | | | | | | | | |
|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 |
| Percent | 0.67 | 3.37 | 8.43 | 14.0 | 17.6 | 17.6 | 14.6 | 10.4 | 6.53 | 3.63 | 1.81 | 0.82 | 0.35 | 0.13 | 0.05 | 0.01 | 0.01 |

The Poisson Distribution provided in Table 1 assumes 100% efficiency of DNA binding with the biological analogue beads. Because 100% efficiency is not achieved in the laboratory, even under the most ideal conditions, an experiment was conducted using five genome equivalents per biological analogue bead, as described below.

Total genomic DNA was prepared from *B. globigii*. The concentration of DNA was determined by optical spectroscopy. The concentration of the silica beads used was provided by the manufacturer of the beads (Bang's Laboratories). The genomic DNA and silica beads were combined such that five genomic equivalents of DNA were provided for each silica bead (see Table 2, below). The attachment of the DNA to the beads was performed by the silica bead manufacturer's recommended protocol (adapted from Tech-Note 302, "Molecular Biology", from Bang's Laboratories, "Nucleic Acid Adsorption to Silica Microspheres"). After attachment was complete, the biological analogue beads were washed nine times using 70% ethanol in order to be absolutely certain all unbound DNA was removed. The beads were stored in the final 70% ethanol wash solution.

The newly-created biological analogue beads were removed from the 70% ethanol and placed in Tris/EDTA buffer (made according to a recipe provided by Bang's Laboratories, 10 mM Tris base, 1 mM EDTA-$Na_2$). The biological analogue beads were then subjected to sonication (to simulate sonication in Cepheid's GenExpert System, part of the NG Biological Detection System). A small aliquot of liquid containing the DNA that was removed from the biological analogue beads during sonication was set aside for analysis by PCR (the PCR analysis described herein was conducted by TaqMan PCR analysis unless otherwise indicated). The biological analogue beads were then centrifuged briefly to pellet the beads, and another liquid aliquot containing DNA was removed for PCR analysis.

PCR analysis indicated that 33% of the DNA was recovered during the extraction step (in which liquid was simply removed from the biological analogue beads after sonication). The beads were then contrifuged and the supernatant analysed. TaqMan analysis of this sample indicated that 29% of the DNA was recovered during the extraction. Removing the biological analogue beads from the liquid by centrifugation did not significantly alter the DNA yield.

approximately 1.5 genome equivalents per biological analogue bead, as indicated in Table 2. This number is close to the average genome equivalents per *B. globigii* endospore.

TABLE 2

Data for Recovery of DNA from Biological analogues.

| Sample | Copies |
|---|---|
| DNA Prep | 5.10E+07 |
| Rinse 3 | 5.30E+05 |
| Rinse 5 | 1.10E+05 |
| Rinse 7 | 4.70E+05 |
| Rinse 9 | 4.60E+05 |
| Extraction 1 | 1.70E+07 |
| Extraction 2 | 1.50E+07 |

This experiment therefore demonstrated that a *B. globigii* biological analogue, constructed in accordance with the teachings of the present invention, is useful as a non-biological surrogate for dissemination-type testing. The use of 2 μm biological analogues, with five genome equivalents per biological analogue, provides a surrogate that quite closely resembles the actual *B. globigii* endospore.

As noted above, *B. globigii* endospores contain one genome copy per endospore. When these endospores are analyzed using the GenExpert System, they are subject to sonication. This breaks open the endospore and releases the DNA, making it available for PCR analysis. The experiment described above demonstrates that the biological analogue of the present invention can be subjected to sonication, that such sonication removes DNA from the biological analogues, and that the DNA so removed is suitable for PCR analysis. Thus, in these respects, the behavior of the biological analogue simulates precisely the behavior of the actual *B. globigii* endospore.

Attachment of genomic DNA to polystyrene beads by streptavidin/biotin interactions The ratio of 5 genome equivalents per bead described above was also used in this embodiment of the present invention. "EZ-Link Psoralin-PEO Biotin" (Pierce Laboratories) was used to biotinylate genomic DNA from Bg. A labeling protocol was developed based on a protocol provided by Pierce Laboratories. Reactions were set up with differing amounts of Psoralin-PEO-Biotin and a constant amount of DNA. The reactions were irradiated with long-wave UV light. The excess Psoralen-PEO-Biotin was removed from the DNA by washing and precipitation steps.

ProActive Microspheres (Bang's Laboratories) were used for the bead component of the biological analogue. The beads were polystyrene and were already coated with streptavidin. Preparation of the beads and attachment of the biotinylated genomic Bg DNA were performed using protocols provided by the manufacturer (Bang's Laboratories). The information was collected from the following literature: TechNotes 101, 203, and 302, which are "ProActive Microspheres", "Washing Microspheres" and "Molecular Biology", respectively.

In summary, the biotinylated DNA prepared above was added to washed polystyrene beads coated with streptavidin. The reactions were allowed to incubate and the beads (now with biotinylated DNA attached) were washed to remove any unbound DNA and stored. Following construction, the biological analogues were analyzed in Cepheid's GenExpert System and were able to be detected. Additional tests were performed to verify that the biological analogues would remain detectable when disseminated from a nebulizer and captured in the SpinCon collector used in Northrup Grumman's Biological Detection System. During testing, the biological analogues were disseminated, captured by the SpinCon, and placed in the GenExpert system and detected.

The preceding examples illustrate potential mechanisms for attaching biomarkers to the beads. It is to be understood that the methods described above are only two examples of a great variety of mechanisms for attachment of biomolecules to the beads. Furthermore, different methods of attachment may be more appropriate for different biomolecules (for example, dipicolinic acid). Additional embodiments of the present invention are also contemplated herein. For instance, a biological analogue can be created having more than one type of biological molecule attached thereto (DNA and protein, for example). Alternatively, a biological analogue could be constructed having biomolecules from different sources attached to the same bead. For instance, a single biological analogue could be created having DNA from both Bg and Eh (*Erwinia herbicola* a plant pathogen). This biological analogue is useful in that it provides a surrogate for both organisms without the use of multiple versions of the product.

In addition, the biological analogues of the present invention can be labeled with synthetic strands of DNA that can identify a specific batch of biological analogues or otherwise trace a biological analogue of interest to a particular sale. Thus, a biological analogue detected with a biological detection system could be traced back to a specific end user or purchaser.

Also, biological analogues could be produced having varying particle sizes. For example, small particle sizes can be produced to mimic weapon-grade biological warfare agents, while larger particle sizes or multiple particle agglomerates may be produced to mimic biological warfare agents that might be used by a less sophisticated organization. It is important to be able to detect both types of particles.

Using microencapsulation techniques, or other methods of coating, biological analogues can be developed that have a very short half-life in the environment in which they are being used. This decreases the likelihood of background biological analogue material confounding the interpretation of subsequent analyses.

Fluorescent biological analogues can be used to mimic the fluorescent activity displayed by various bacteria. NAD/NADH$_2$ can be incorporated into the biological analogues for this type of testing.

Biological analogues can also be produced in dry preparations for simulating spores found, for example, in postal envelopes. The biological analogues can be dispensed into dry envelopes and run through the postal machinery to evaluate the capability of the Biological Detection System to detect "spiked" envelopes. This is useful for an inspector performing 'spot checks' of a postal facility. The dry biological analogue material could be produced in different particle sizes to reflect different degrees of sophistication on the part of those who might use actual biological weapon agents.

Also, biological analogues can be developed to mimic a protein of interest (a protein toxin, for example). To accomplish this, purified protein is subjected to proteolysis rendering it harmless. The fragments may then be attached to the beads or formed into particles in the required size range. The biological analogues are then disseminated, collected, and analyzed by, for instance, ELISA-based methods or pyrolysis mass spectrometer.

Biological particles such as *Bacillus anthracis*, can be made nonviable through physical techniques such as autoclaving, french pressure cell, or sonication. Other techniques such as proteolysis may also be employed to render the particle harmless. In the process, under most conditions, the particles will be fragmented. These fragments may then be attached to beads or formed into particles, of the same aerodynamic diameter as the biological parcel, in the laboratory or during dissemination. Through these processes, biological analogues can be engineered to look like actual organisms to pyrolysis mass spectrometer detections systems and other systems that key on specific chemical constituents. A specific example would be to take a suspension, of a known concentration of *Bacillus anthracis*, autoclave it, cool it, and adjust the concentration by adding water or evaporating liquid off of the suspension. The concentration would be adjusted so that dissemination of the fragments will cause agglomerations to form in the size range of the *Bacillus anthracis*. The size distribution of the formed biological analogues will be determined by the size of the cell fragments and the number of fragments in each droplet formed during dissemination.

In addition to the various embodiments of the present invention that can be produced, the usefulness of the present invention is not limited to testing or calibrating detection systems for biological warfare agents. Additional uses are described below, and it is contemplated that many other uses will be readily apparent to one of skill in the art upon reading this disclosure.

Non-military or weapons-related uses are also evident. Airborne biological organisms, toxins and allergens, such as Legionnaire's disease, toxic molds, and pollen, can cause serious illness and even death. Legionnaire's disease, for instance, is caused by the naturally occurring *Legionella pneumophila* bacterium and its related serotypes. The dissemination of this organism and its transmission to humans is not well-understood, but it is known to involve inhalation of aerosolized water droplets containing viable *Legionella* that are deposited in the lungs, causing infection. Cooling towers, faucet nozzles, aerators, piping leaks, and showerheads have been discovered to create such *Legionella*-containing aerosols. Biological analogues can be used to mimic *Legionella* in a building's water system and aerosol production scenarios could be undertaken to realistically simulate a contamination and dissemination event for study. Similarly, bacterial, viral, mold and pollen biological analogues can be customized and used to study indoor air-quality, define standards, and test monitoring equipment.

Further uses are evident in the food industry. Food processing plants are required to prepare Hazard Analysis Critical Control Point (HACCP) prevention plans. These plans are specific to a processing plant, the types of food produced, and the various ways in which the food can become contaminated with disease-causing organisms such as *Escherichia coli, Listeria monocytogenes, Clostridium botulinum*, and *Salmonella spp.*, for example. Testing HACCP plans is difficult because the risk of introducing live microorganisms is unacceptable. For testing transport and dissemination of contaminant organisms in the food processing environment (air, water, surfaces, and plant operators), biological analogues can be constructed to mimic organisms of concern and then introduced into the plant processes at risk analysis points. The plant can then be operated and monitored for the presence of the biological analogues and biocontrol procedures can be evaluated.

It is understood that the invention is not limited to the specific details described herein, which are given by way of example only, and that various modifications and alterations, including use of other potential and yet-to-be discovered methods of attachment of any and all biomolecule of choice, are possible without departing from the spirit or scope of the invention as defined in the claims.

The invention claimed is:

1. A biological analogue for use in testing or calibrating a detection system for detecting *Bacillus globigii* comprising:
   a) a first portion, said first portion being a bead; and
   b) a DNA portion carried by said first portion;
   wherein said biological analogue is aerosolized, and further wherein said biological analogue acts as a surrogate for said *Bacillus globigii*, and said detection system recognizes said biological analogue as *Bacillus globigii*.

2. The biological analogue of claim 1 wherein said DNA portion is total genomic *Bacillus globigii* DNA.

3. The biological analogue of claim 1 where in said first portion is selected from the group consisting latex beads, polystyrene beads, silica beads, polystyrene beads, styrene/divinylbenzne copolymer beads, polymethylmethcarylate beads, polyvinyltoluence beads, styrene/butadiene copolymer beads, styrene/vinyltoluene copolymer beads, vinyl carboxylic acid/styrene copolymer beads, and styrene/maleic anhydride copolymer beads, amino-modified microsphere beads, and carboxylate-modified microsphere beads, and paramagnetic beads.

4. The biological analogue of claim 1 wherein said DNA portion is carried by said first portion because of a linkage selected from the group consisting of covalent linkages, ionic linkages, and streptavidin/biotin linkages.

5. A biological analogue for use in testing or calibrating a detection system for detecting a biological material comprising:
   a) a first portion which is a polystyrene bead with an aerodynamic diameter approximately the same as said biological material; and
   b) a second portion carried by said first portion, wherein the second portion is genomic *Bacillus globigii* DNA;
   wherein said biological analogue tests or calibrates said detection system by acting as a surrogate for said biological material, and further wherein said detection system recognizes said biological analogue as said biological material.

6. The biological analogue of claim 5 herein said second portion is carried by said first portion because of a streptavidin/biotin linkage.

7. The biological analogue of claim 5 wherein an average of 1–3 genome equivalents of *Bacillus globigii* genomic DNA are attached per first portion.

8. A biological analogue for use in testing or calibrating a detection system for detecting a biological material comprising:
   a) a first portion which is a polystyrene bead with approximately the same aerodynamic diameter as *Bacillus anthracis*; and
   b) a second portion carried by said first portion, wherein the second portion is genomic *Bacillus globigii* DNA;
   wherein said biological analogue tests or calibrates said detection system by acting as a surrogate for said biological material, and further wherein said detection system recognizes said biological analogue as said biological material.

9. The biological analogue of claim 8 wherein an average of 1–3 genome equivalents of *Bacillus globigii* genomic DNA are attached per first portion.

10. The biological analogue of claim 8 wherein said second portion is carried by said first portion because of a streptavidin/biotin linkage.

11. A biological analogue for use in testing or calibrating a detection system for detecting a biological material wherein said biological material is *Bacillus globigii* comprising:
    a) a first portion, wherein said first portion is a bead; and
    b) a second portion carried by said first portion, wherein said second portion is selected from the group consisting of DNA, RNA, PNA, and a protein;
    wherein said biological analogue is aerosolized, and further wherein said biological analogue tests or calibrates said detection system by acting as a surrogate for said biological material, and said detection system recognizes said biological analogue as said biological material.

12. The biological analogue of claim 11 wherein said second portion is DNA.

13. The biological analogue of claim 11 wherein said second portion is RNA.

14. The biological analogue of claim 11 wherein said second portion is PNA.

15. The biological analogue of claim 11 wherein said second portion is protein.

16. A biological analogue for use in testing or calibrating a detection system for detecting a biological material, wherein said biological material is *Bacillus anthracis* comprising:
    a) a first portion, wherein said first portion is a bead; and
    b) a second portion carried by said first portion, wherein said second portion is selected from the group consisting of DNA, RNA, PNA, and a protein;
    wherein said biological analogue is aerosolized, and further wherein said biological analogue tests or calibrates said detection system by acting as a surrogate for said biological material, and said detection system recognizes said biological analogue as said biological material.

17. The biological analogue of claim 16 wherein said second portion is DNA.

18. The biological analogue of claim 16 wherein said second portion is RNA.

19. The biological analogue of claim 16 wherein said second portion is PNA.

20. The biological analogue of claim 16 wherein said second portion is protein.

21. A biological analogue for use in testing or calibrating a detection system for detecting a biological material, wherein said biological material is *Yersinia pestis* comprising:
   a) a first portion, wherein said first portion is a bead; and
   b) a second portion carried by said first portion, wherein said second portion is selected from the group consisting of DNA, RNA, PNA, and a protein;
   wherein said biological analogue is aerosolized, and further wherein said biological analogue tests or calibrates said detection system by acting as a surrogate for said biological material, and said detection system recognizes said biological analogue as said biological material.

22. The biological analogue of claim 21 wherein said second portion is DNA.

23. The biological analogue of claim 21 wherein said second portion is RNA.

24. The biological analogue of claim 21 wherein said second portion is PNA.

25. The biological analogue of claim 21 wherein said second portion is protein.

26. A biological analogue for use in testing or calibrating a detection system for detecting a biological material, wherein said biological material is *Orthopoxvirus* comprising:
   a) a first portion, wherein said first portion is a bead; and
   b) a second portion carried by said first portion, wherein said second portion is selected from the group consisting of DNA, RNA, PNA, and a protein;
   wherein said biological analogue is aerosolized, and further wherein said biological analogue tests or calibrates said detection system by acting as a surrogate for said biological material, and said detection system recognizes said biological analogue as said biological material.

27. The biological analogue of claim 26 wherein said second portion is DNA.

28. The biological analogue of claim 26 wherein said second portion is DNA.

29. The biological analogue of claim 26 wherein said second portion is DNA.

30. The biological analogue of claim 26 wherein said second portion is DNA.

31. A biological analogue for use in testing or calibrating a detection system for detecting a biological material, wherein said biological material is *Salmonella* comprising:
   a) a first portion, wherein said first portion is a bead; and
   b) a second portion carried by said first portion, wherein said second portion is selected from the group consisting of DNA, RNA, PNA, and a protein;
   wherein said biological analogue is aerosolized, and further wherein said biological analogue tests or calibrates said detection system by acting as a surrogate for said biological material, and said detection system recognizes said biological analogue as said biological material.

32. The biological analogue of claim 31 wherein said second portion is DNA.

33. The biological analogue of claim 31 wherein said second portion is RNA.

34. The biological analogue of claim 31 wherein said second portion is PNA.

35. The biological analogue of claim 31 wherein said second portion is protein.

* * * * *